United States Patent [19]
Arias

[11] Patent Number: 5,878,759
[45] Date of Patent: Mar. 9, 1999

[54] DENTAL FLOSS TOOL

[76] Inventor: Denis Arias, 15 Washington St., Belleville, N.J. 07109

[21] Appl. No.: 870,033

[22] Filed: Jun. 5, 1997

[51] Int. Cl.[6] .................................................. A61C 15/00
[52] U.S. Cl. ............................................ 132/325; 132/326
[58] Field of Search ................................... 132/322, 323, 132/324, 325, 326, 327

[56] References Cited

U.S. PATENT DOCUMENTS

| | | | |
|---|---|---|---|
| 3,835,872 | 9/1974 | Daniel | 132/324 |
| 3,998,236 | 12/1976 | Koo | 132/324 |
| 4,307,740 | 12/1981 | Florindez et al. | 132/322 |
| 4,326,549 | 4/1982 | Hinding | 132/322 |
| 5,176,157 | 1/1993 | Mazza | 132/325 |
| 5,232,002 | 8/1993 | McClallen | 132/325 |
| 5,495,863 | 3/1996 | Bergman | 132/326 |

FOREIGN PATENT DOCUMENTS

| 4241576 | 6/1994 | Germany | 132/322 |
|---|---|---|---|
| 9011057 | 10/1990 | WIPO | 132/322 |

*Primary Examiner*—Todd E. Manahan

[57] ABSTRACT

A new Dental Floss Tool for orienting and securing a length of dental floss in a convenient to use manner. The inventive device includes a handle piece, an intermediate piece joined to and extending from the handle piece, and a head piece joined to and extending from the intermediate piece wherein the head piece includes a pair of spaced tines extending therefrom. Furthermore, a spool of dental floss is positioned within the handle piece. A working length of the dental floss extends from the handle piece and passes along the intermediate piece towards the head piece, across the pair of spaced tines, back towards the intermediate piece, and around a take-up wheel. While passing along the intermediate piece, the dental floss passes through an actuator button which, when actuated, causes the dental floss spanning the pair of spaced tines to move laterally.

19 Claims, 6 Drawing Sheets

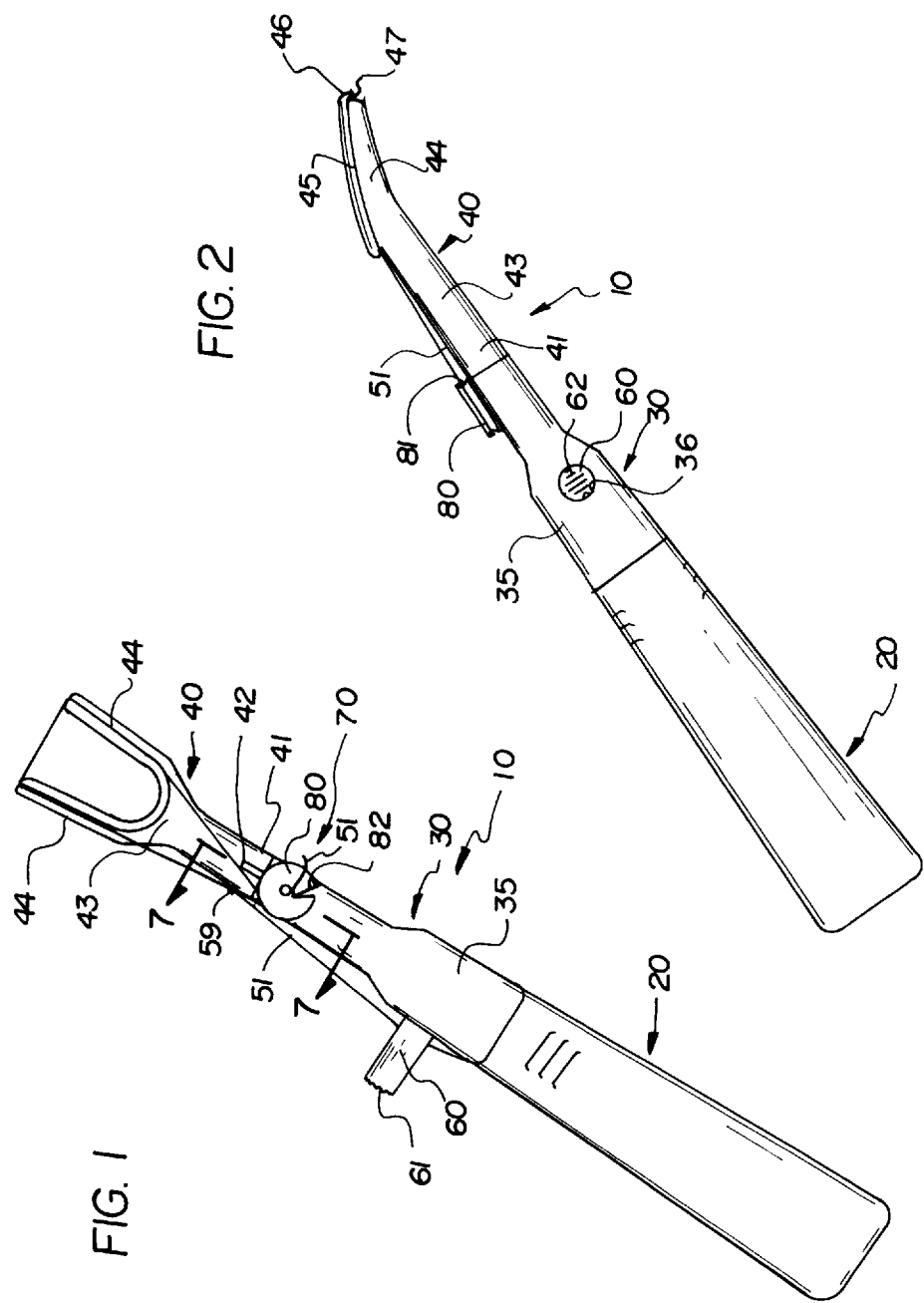

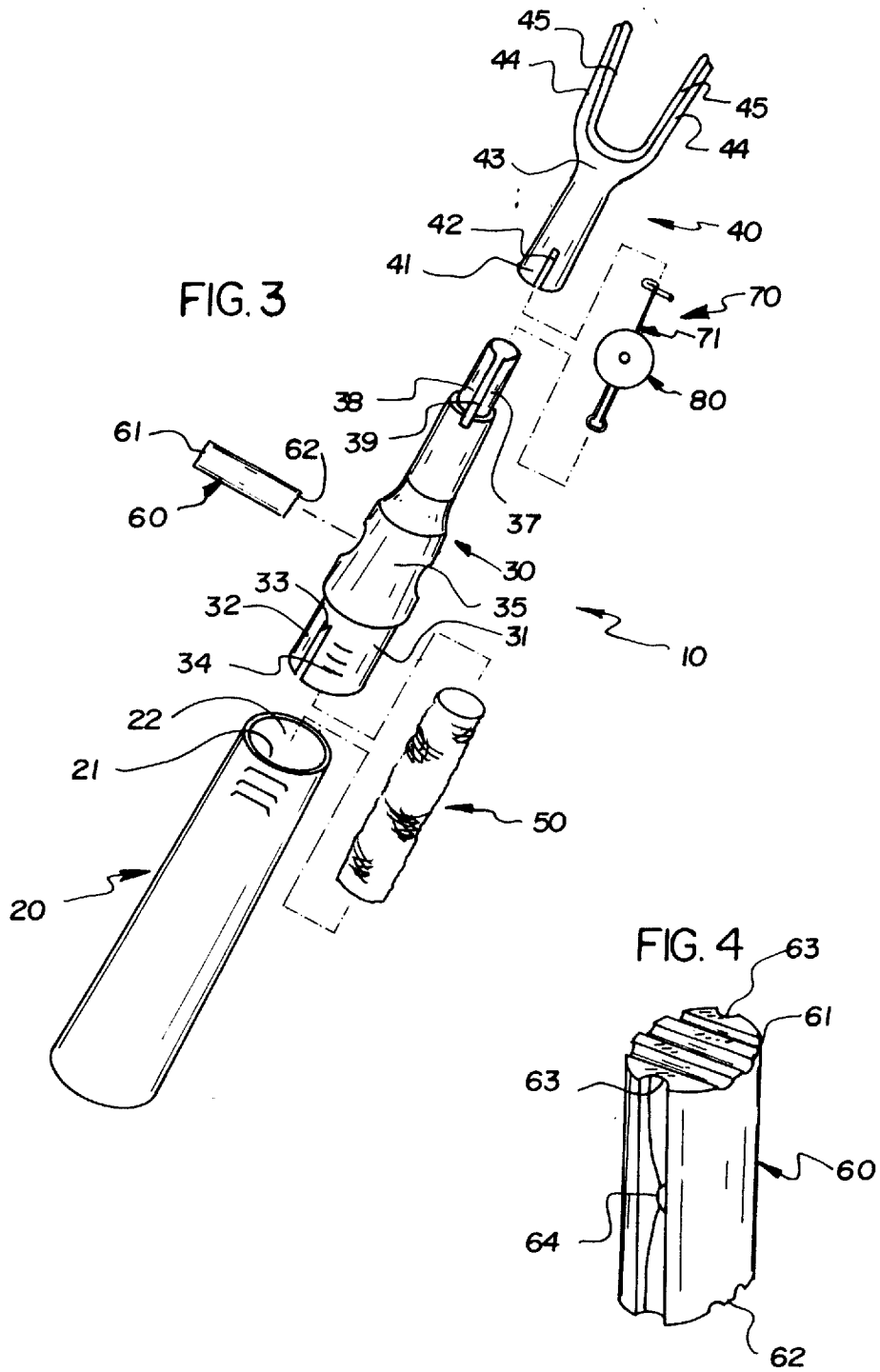

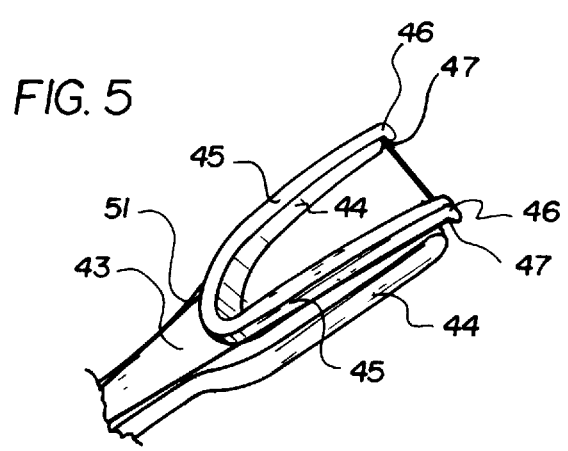
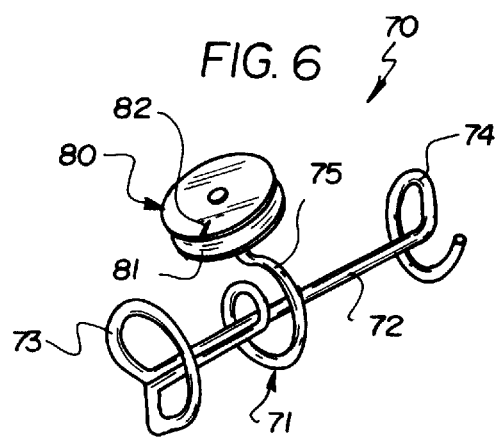

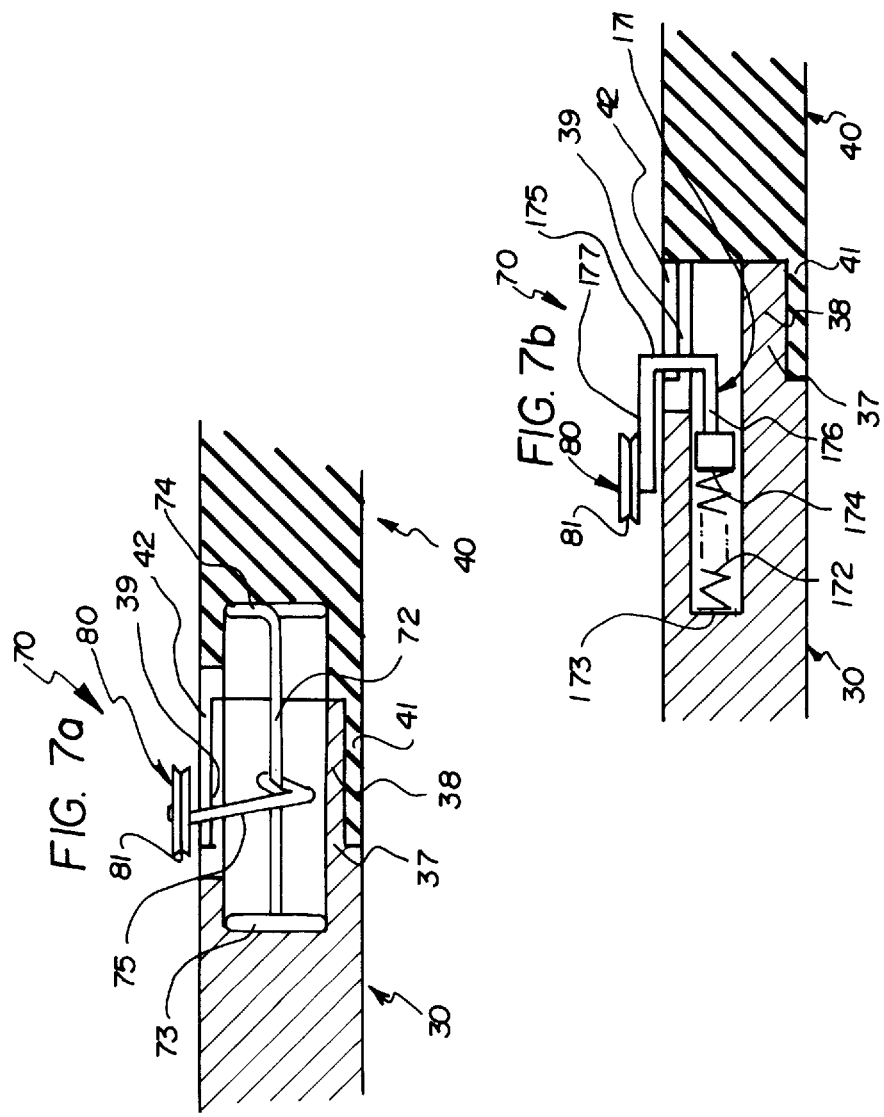

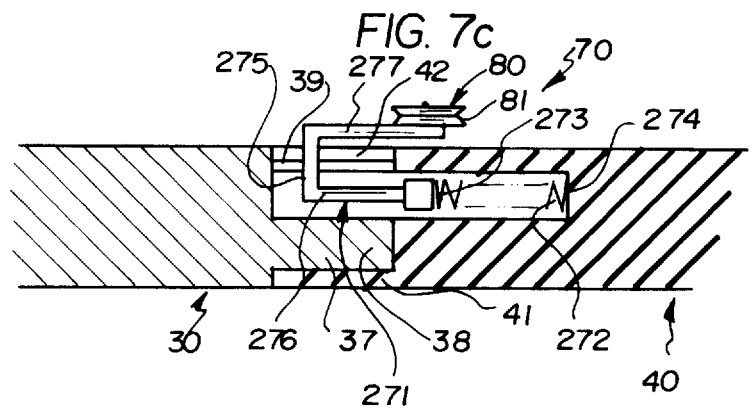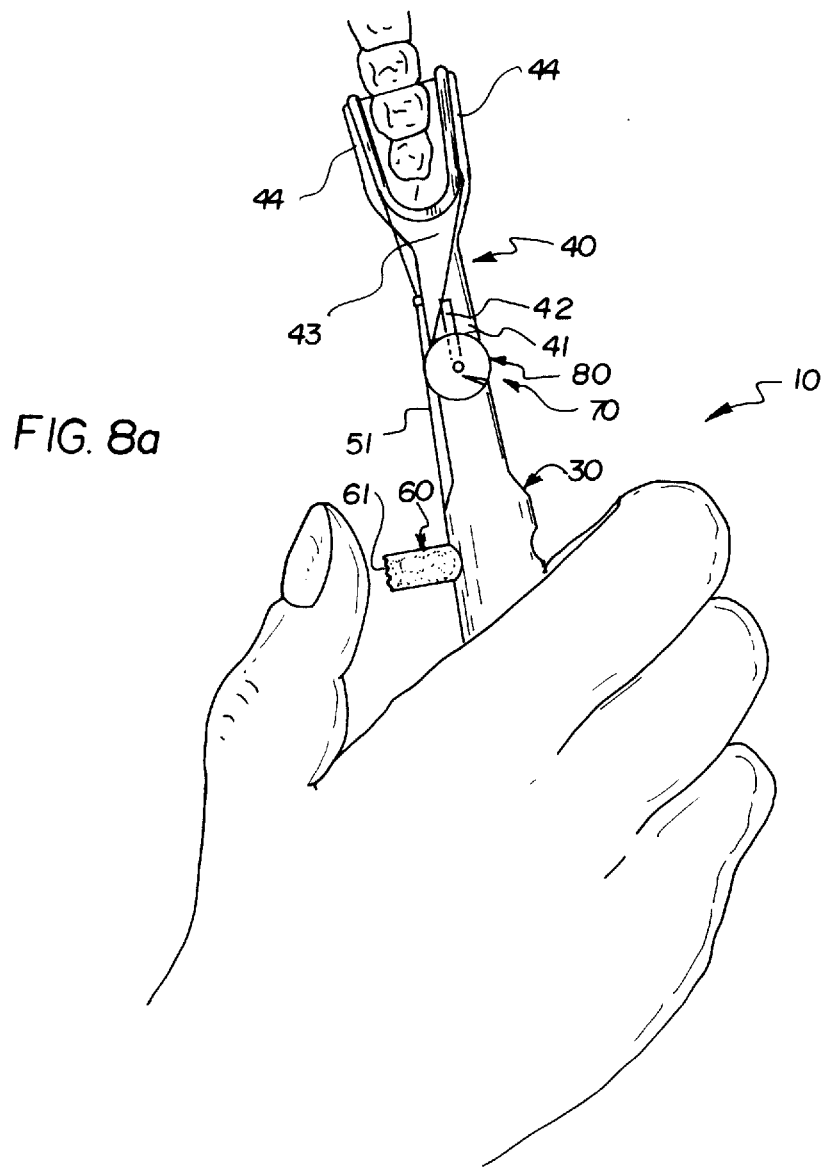

DENTAL FLOSS TOOL

BACKGROUND OF THE INVENTION

1. Field of the Invention

The present invention relates to dental floss holding and positioning tools and more particularly pertains to a new Dental Floss Tool for orienting and securing a length of dental floss in a convenient to use manner.

2. Description of the Prior Art

The use of dental floss holding and positioning tools is known in the prior art. More specifically, dental floss holding and positioning tools heretofore devised and utilized are known to consist basically of familiar, expected and obvious structural configurations, notwithstanding the myriad of designs encompassed by the crowded prior art which have been developed for the fulfillment of countless objectives and requirements.

Known prior art dental floss holding and positioning tools include U.S. Pat. No. 5,417,232; U.S. Pat. No. 5,423,338; U.S. Pat. No. D354,154; U.S. Pat. No. 5,450,866; U.S. Pat. No. 4,518,000; U.S. Pat. No. 4,151,851; U.S. Pat. No. 4,006,750; and U.S. Pat. No. D301,071.

While these devices fulfill their respective, particular objectives and requirements, the aforementioned patents do not disclose a new Dental Floss Tool. The inventive device includes a handle piece, an intermediate piece joined to and extending from the handle piece, and a head piece joined to and extending from the intermediate piece wherein the head piece includes a pair of spaced tines extending therefrom. Furthermore, a spool of dental floss is positioned within the handle piece. A working length of the dental floss extends from the handle piece and passes along the intermediate piece towards the head piece, across the pair of spaced tines, back towards the intermediate piece, and around a take-up wheel. While passing along the intermediate piece, the dental floss passes through an actuator button which, when actuated, causes the dental floss spanning the pair of spaced tines to move laterally.

In these respects, the Dental Floss Tool according to the present invention substantially departs from the conventional concepts and designs of the prior art, and in so doing provides an apparatus primarily developed for the purpose of orienting and securing a length of dental floss in a convenient to use manner.

SUMMARY OF THE INVENTION

In view of the foregoing disadvantages inherent in the known types of dental floss holding and positioning tools now present in the prior art, the present invention provides a new Dental Floss Tool construction wherein the same can be utilized for orienting and securing a length of dental floss in a convenient to use manner.

The general purpose of the present invention, which will be described subsequently in greater detail, is to provide a new Dental Floss Tool apparatus and method which has many of the advantages of the dental floss holding and positioning tools mentioned heretofore and many novel features that result in a new Dental Floss Tool which is not anticipated, rendered obvious, suggested, or even implied by any of the prior art dental floss holding and positioning tools, either alone or in any combination thereof.

To attain this, the present invention generally comprises a handle piece, an intermediate piece joined to and extending from the handle piece, and a head piece joined to and extending from the intermediate piece wherein the head piece includes a pair of spaced tines extending therefrom. Furthermore, a spool of dental floss is positioned within the handle piece. A working length of the dental floss extends from the handle piece and passes along the intermediate piece towards the head piece, across the pair of spaced tines, back towards the intermediate piece, and around a take-up wheel. While passing along the intermediate piece, the dental floss passes through an actuator button which, when actuated, causes the dental floss spanning the pair of spaced tines to move laterally.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature an essence of the technical disclosure of the application. The abstract is neither intended to define the invention of the application, which is measured by the claims, nor is it intended to be limiting as to the scope of the invention in any way.

It is therefore an object of the present invention to provide a new Dental Floss Tool apparatus and method which has many of the advantages of the dental floss holding and positioning tools mentioned heretofore and many novel features that result in a new Dental Floss Tool which is not anticipated, rendered obvious, suggested, or even implied by any of the prior art dental floss holding and positioning tools, either alone or in any combination thereof.

It is another object of the present invention to provide a new Dental Floss Tool which may be easily and efficiently manufactured and marketed.

It is a further object of the present invention to provide a new Dental Floss Tool which is of a durable and reliable construction.

An even further object of the present invention is to provide a new Dental Floss Tool which is susceptible of a low cost of manufacture with regard to both materials and labor, and which accordingly is then susceptible of low prices of sale to the consuming public, thereby making such Dental Floss Tool economically available to the buying public.

Still yet another object of the present invention is to provide a new Dental Floss Tool which provides in the apparatuses and methods of the prior art some of the advantages thereof, while simultaneously overcoming some of the disadvantages normally associated therewith.

Still another object of the present invention is to provide a new Dental Floss Tool for orienting and securing a length of dental floss in a convenient to use manner.

Yet another object of the present invention is to provide a new Dental Floss Tool which includes a handle piece, an intermediate piece joined to and extending from the handle piece, and a head piece joined to and extending from the intermediate piece wherein the head piece includes a pair of spaced tines extending therefrom. Furthermore, a spool of dental floss is positioned within the handle piece. A working length of the dental floss extends from the handle piece and passes along the intermediate piece towards the head piece, across the pair of spaced tines, back towards the intermediate piece, and around a take-up wheel. While passing along the intermediate piece, the dental floss passes through an actuator button which, when actuated, causes the dental floss spanning the pair of spaced tines to move laterally.

Still yet another object of the present invention is to provide a new Dental Floss Tool that would make the process of flossing easier, more economical, more sanitary, and more convenient. Commonly, a user of dental floss merely holds a length of dental floss with his or her fingers and often wraps the ends of the dental floss around their fingers. This method is wasteful of dental floss and, furthermore, is somewhat difficult and awkward. Accordingly, the present invention would provide firm control of the dental floss and would allow a user thereof to floss without having to insert his or her fingers into their mouth.

Even still another object of the present invention is to provide a new Dental Floss Tool that can be operated with one hand.

Even still another object of the present invention is to provide a new Dental Floss Tool that would provide a user thereof with more control of the dental floss thereby possibly eliminating the incidence of improper flossing techniques.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a top view of the present invention.

FIG. 2 is a side view thereof.

FIG. 3 is an exploded isometric illustration of the present invention.

FIG. 4 is an isometric illustration of the actuator button of the present invention.

FIG. 5 is an isometric illustration of the pair of spaced tines of the head piece of the present invention.

FIG. 6 is an isometric illustration of a first embodiment of the tensioning means of the present invention.

FIGS. 7a, 7b, and 7c are cross sectional views taken along line 7—7 of FIG. 1.

FIG. 7a is a cross sectional illustration of the first embodiment of the tensioning means of the present invention.

FIG. 7b is a cross sectional illustration of a second embodiment of the tensioning means of the present invention.

FIG. 7c is a cross sectional illustration of a third embodiment of the tensioning means of the present invention.

FIGS. 8a and 8b are illustrations of the present invention in use.

DESCRIPTION OF THE PREFERRED EMBODIMENT

Figure 8B:
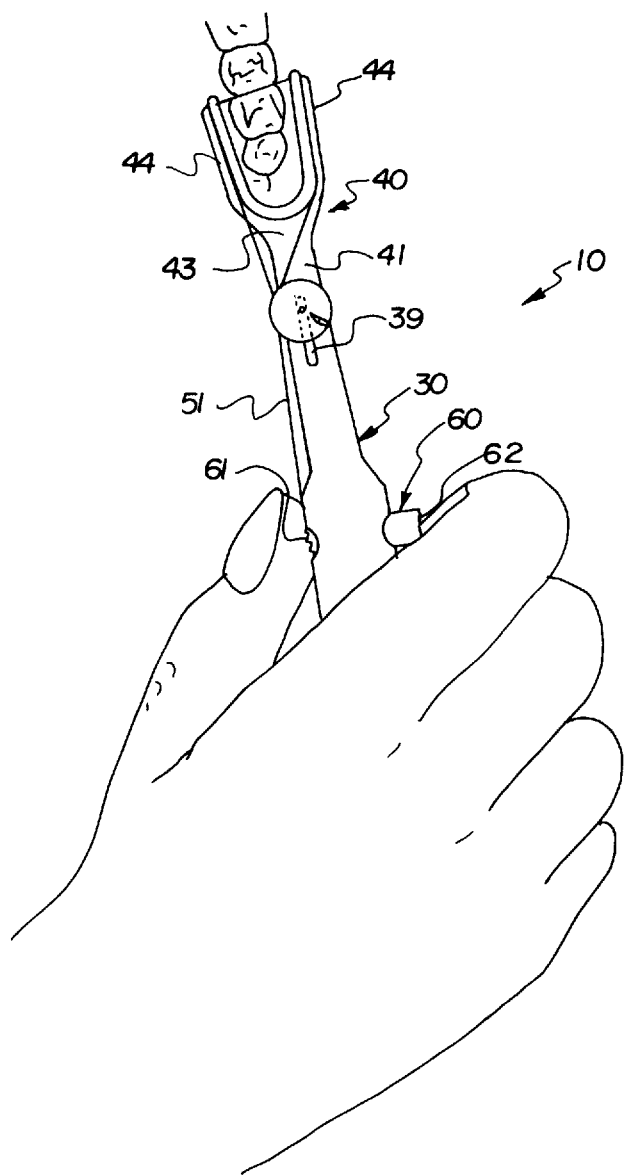

With reference now to the drawings, and in particular to FIGS. 1 through 8 thereof, a new Dental Floss Tool embodying the principles and concepts of the present invention and generally designated by the reference numeral 10 will be described.

As best illustrated in FIGS. 1 through 8, the Dental Floss Tool 10 comprises a handle piece 20, an intermediate piece 30 joined to and extending from the handle piece 20, and a head piece 40 joined to and extending from the intermediate piece 30 wherein the head piece 20 includes a pair of spaced tines 44 extending therefrom. Furthermore, a spool of dental floss 50 is positioned within the handle piece 20. A working length 51 of the dental floss 50 extends from the handle piece 20 and passes along the intermediate piece 30 towards the head piece 40, across the pair of spaced tines 44, back towards the intermediate piece 30, and around a take-up wheel 80. While passing along the intermediate piece 30, the dental floss 50 passes through an actuator button 60 which, when actuated, causes the dental floss 50 spanning the pair of spaced tines 44 to move laterally.

The handle piece 20 has a hollow interior 21 and has an open end 22. The handle piece 20 includes a node (not shown) provided on an inner surface within the open end 22 thereof.

The intermediate piece 30 has a first end 31, a second end 37, and an intermediate portion 35 therebetween. A first neck portion 32 is provided at the first end 31 and a second neck portion 38 is provided at the second end 37. As such, the first neck portion 32 slidingly engages and fits within the open end 22 of the handle piece 20.

The first neck portion 32 and the second neck portion 38 are each open to the first end 31 and the second end 37, respectively. Furthermore, the first neck portion 32 and the second neck portion 38 each have a slot 33 and 39, respectively, therein.

The first neck portion 32 includes a plurality of spaced nodes 34 provided on an outer surface thereof (FIG. 3). Accordingly, when the first neck portion 32 of the intermediate piece 30 is fitted within the open end 22 of the handle piece 20, the node (not shown) provided within the open end 22 of the handle piece 20 interferentially engages the plurality of spaced nodes 34 provided on the first neck portion 32. As such, the open end 22 of the handle piece 20 may be stagingly positioned along the first neck portion 32.

The intermediate portion 35 of the intermediate piece 30 has a bore 36 therethrough. An actuator button 60, having a first end 61 and a second end 62, is slidingly fitted within the bore 36. The actuator button 60 may be moved between a protruding position wherein the first end 61 of the actuator button 60 perpendicularly protrudes from the intermediate piece 30 and a flush position wherein the first end 61 of the actuator button 60 is generally flush with the intermediate piece 30.

The actuator button 60 has a pair of grooves 63 in opposite sides thereof and has a hole 64 laterally therethrough intermediate the first end 61 and second end 62 (FIG. 4). Accordingly, the hole 64 interconnects the pair of grooves 63. As such, the hole 64 is exposed when the actuator button 60 is in the protruding position and is concealed when the actuator button 60 is in the flush position.

The head piece 40 has a first end 41 and a second end 43 and includes a pair of spaced tines 44 extending from the second end 43. The pair of spaced tines 44 are oriented at an oblique angle to the handle piece 20.

The head piece 40 is open at the first end 41 and includes a slot 42 in the first end 41 thereof. As such, the second neck portion 38 of the intermediate piece 30 slidingly engages and fits within the first end 41 of the head piece such that the slot 39 in the second neck portion 38 is aligned and communicates with the slot 42 in the head piece 40.

As best illustrated in FIG. 5, each of the pair of spaced tines 44 includes a shoulder 45 extending therealong. Furthermore, each of the tines 44 has a tip end 46 wherein each tip end 46 has a notch 47 therein. As such, the working length 51 of dental floss 50 passes down one tine 44, abutting the shoulder 45 thereof, through the notch 47 of each of the tines 44, and up the other tine 44, abutting the shoulder 45 thereof. Accordingly, a section of the dental floss 50 spans the pair of spaced tines 44.

To prevent the working length 51 of the dental floss 50 from hanging loosely, a guide eye 59 is provided along the path thereof. As such, guides eyes 59 may be provide on the intermediate piece 30 and the head piece 40. Accordingly, the working length 51 of the dental floss 50 passes through the guide eyes 59.

A tensioning means 70 is provided for holding the working length 51 of dental floss 50 in tension. The tensioning means 70 comprises a spring assembly 71 positioned within the second neck portion 38 of the intermediate piece 30, and a take-up wheel 80 coupled to the spring assembly 71. The take-up wheel 80 has a perimetrical groove 81 therein in which the working length 51 of the dental floss 50 is wound. In addition, the take-up wheel 80 includes a notch 82 therein communicating with the perimetrical groove 81. The notch 82 includes a sharp edge 83 for severing a length of the dental floss 50.

In a first embodiment, illustrated in FIGS. 6 and 7a, the spring assembly 71 comprises a torsional rod 72 having a first end 73 positioned within the second neck portion 38 of the intermediate piece 30 and a second end 74 positioned within the first end 41 of the head piece 40. The torsional rod 72 includes an arm 75 extending through the slot 39 in the second neck portion 38 and the slot 42 in the first end 41 of the head piece 40. As such, the take-up wheel 80 is mounted to the end of the arm 75.

In the first embodiment, the arm 75 of the torsional rod 72 is biased away from the head piece 40. Accordingly, when the working length 51 of the dental floss 50 is wound around the take-up wheel 80, the arm 75 imposes tension on the dental floss 50. When the actuator button 60 is pressed and moved to the flush position, the working length 51 of the dental floss 50 is effectively pulled towards the intermediate piece 30. Accordingly, tension in the working length 51 of the dental floss 50 increases whereby the arm 75 of the torsional rod 72 is pulled towards the head piece 40. When the actuator button 60 is released, the arm 75 returns to its biased position wherein the dental floss 50 is effectively pulled away from the intermediate piece 30 such that the actuator button 60 moves to the protruding position.

In a second embodiment, illustrated in FIG. 7b, the spring assembly 171 comprises a helical compression spring 172 disposed within the second neck portion 38 of the intermediate piece 30, and a generally U-shaped member 175 interconnecting the helical compression spring 172 and the take-up wheel 80. The helical compression spring 172 has a first end 173 and a second end 174 wherein the first end 173 is secured within the second end 37 of the intermediate piece 30. The U-shaped member 175 has a first leg 176 and a second leg 177. The first leg 176 is disposed within the second neck portion 38 of the intermediate piece 30 and joined to the second end 174 of the helical compression spring 172. The second leg 177 extends through the slot 39 in the second neck portion 38 and the slot 42 in the first end 41 of the head piece 40. As such, the take-up wheel 80 is mounted to the second leg 177 of the U-shaped member 175.

In the second embodiment, the take-up wheel 80 is biased away from the head piece 40 by the helical compression spring 172 and the U-shaped member 175. Accordingly, when the working length 51 of the dental floss 50 is wound around the take-up wheel 80, the helical compression spring 172 resists expansion and imposes tension on the dental floss 50.

In a third embodiment, illustrated in FIG. 7c, the spring assembly 271 comprises a helical tension spring 272 disposed within the first end 41 of the head piece 40, and a generally U-shaped member 275 interconnecting the helical tension spring 272 and the take-up wheel 80. The helical tension spring 272 has a first end 273 and a second end 274 wherein the second end 274 is confined within the first end 41 of the head piece 40. The U-shaped member 275 has a first leg 276 and a second leg 277. The first leg 276 is disposed within the first end 41 of the head piece 40 and abuts the first end 273 of the helical tension spring 272. The second leg 277 extends through the slot 39 in the second neck portion 38 and the slot 42 in the first end 41 of the head piece 40. As such, the take-up wheel 80 is mounted to the second leg 277 of the U-shaped member 25.

In the third embodiment, the take-up wheel 80 is biased away from the head piece 40 by the helical tension spring 272 and the U-shaped member 275. Accordingly, when the working length 51 of the dental floss 50 is wound around the take-up wheel 80, the helical tension spring 272 resists compression and imposes tension on the dental floss 50.

In use, the spool of dental floss 50 is positioned within the handle piece 20. A free end of the dental floss 50 is passed through the slot 33 provided in the first neck portion 32 of the intermediate piece 30, along the intermediate piece 30 towards the head piece 40, across the pair of spaced tines 44 of the head piece 40, back towards the intermediate piece 30, and around the take-up wheel 80. While passing along the intermediate portion 35 of the intermediate piece 30, the free end of the dental floss 50 is passed through the hole 64 in the actuator button 60. The handle piece 20 and the intermediate piece 30 are joined together wherein the dental floss 50 is captured between the junction of the handle piece 20 and the intermediate piece 30.

As best illustrated in FIGS. 8a and 8b, the user grasps the Dental Floss Tool 10 by placing his or her thumb and forefinger on opposite sides of the intermediate piece 30. As such, the actuator button 60 is actuated by the user's thumb. The user inserts the head piece 40 into his or her mouth and places the section of dental floss 50 spanning the pair of spaced tines 44 between his or her teeth.

Thereafter, the user presses the actuator button 60 so as to move the actuator button 60 to the flush position.

Accordingly, the dental floss 50 spanning the pair of spaced tines 44 moves laterally in a first direction. When the user releases the actuator button 60, the tensioning means 70 causes the dental floss 50 spanning the pair of spaced tines 44 to move laterally in a second direction, opposite the first direction. Accordingly, the actuator button 60 returns to the protruding position. Thereafter, the user removes the section of dental floss 50 from between his or her teeth.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A dental floss tool, comprising:

a handle piece;

an intermediate piece axially extending from said handle piece;

a head piece axially extending from said intermediate piece, said head piece including a pair of spaced tines extending therefrom; a spool of dental floss disposed within said handle piece, a working length of said dental floss extending from said spool;

a tensioning means for holding said working length of said dental floss in tension, said tensioning means comprising a spring assembly mounted in association with at least one of said intermediate piece and said head piece and a take-up wheel coupled to said spring assembly;

said take-up wheel having a perimetrical groove therein said working length of said dental floss wound around said take-up wheel within said perimetrical groove said take-up wheel including a notch therein communicating with said perimetrical groove, said notch including a sharp edge for severing said dental floss;

said working length of said dental floss extending out of said handle piece, along said intermediate piece to said head piece, across said pair of spaced tines of said head piece, and back toward said intermediate piece to said tensioning means; and an actuator means for effectuating movement of said working length of said dental floss.

2. The dental floss tool of claim 1, wherein said intermediate piece has a bore therein, wherein said actuator means comprises:

an actuator button slidingly, fitted within said bore in said intermediate piece, said actuator button having a hole laterally therethrough, said actuator button movable between a protruding position wherein an end of said actuator button perpendicularly protrudes from said intermediate piece and a flush position wherein said end of said actuator button is generally flush with said intermediate piece, wherein said working length of said dental floss passes through said hole in said actuator button, and wherein said working length of said dental floss moves in a first direction when said actuator button is moved to said flush position and moves in a second direction when said actuator button is moved to said protruding position, said second direction opposite said first direction.

3. The dental floss tool of claim 1, wherein each of said pair of spaced tines includes a shoulder extending therealong, wherein each of said pair of spaced tines has a tip end, said tip end having a notch therein, and wherein said working length of said dental floss extends down a first of said pair of spaced tines so as to abut said shoulder thereof, through said notch in said tip end of said first of said pair of spaced tines, across to a second of said pair of spaced tines, through said notch in said tip end of said second of said pair of spaced tines, and up said second of said pair of spaced tines so as to abut said shoulder thereof.

4. The dental floss tool of claim 1, wherein said intermediate piece and said head piece each have a slot therein, said slot in said intermediate piece aligned and communicating with said slot in said head piece, wherein said spring assembly comprises:

a torsional rod having a first end positioned within said intermediate piece and a second end positioned within said head piece, said torsional rod including an arm, said arm projecting through said slot in said intermediate piece and said slot- in said head piece, and wherein said take-up wheel is mounted to said arm.

5. The dental floss tool of claim 1, wherein said intermediate piece and said head piece each have a slot therein, said slot in said intermediate piece aligned and communicating with said slot in said head piece, wherein said spring assembly comprises:

a helical compression spring disposed within said intermediate piece, said helical compression spring having a first end and a second end, said first end secured within said intermediate piece, and a generally U-shaped member having a first leg and a second leg, said first leg disposed within said intermediate piece and joined to said second end of said helical compression spring, said second leg extending through said slot in said intermediate piece and said slot in said head piece, and wherein said take-up wheel is mounted to said second leg of said U-shaped member.

6. The dental floss tool of claim 1, wherein said intermediate piece and said head piece each have a slot therein, said slot in said intermediate piece aligned and communicating with said slot in said head piece, wherein said spring assembly comprises:

a helical tension spring disposed within said head piece, said helical tension spring having a first end and a second end, said second end confined within said head piece, and a generally U-shaped member having a first leg and a second leg, said first leg disposed within said head piece and abutting said first end of said helical tension spring, said second leg extending through said slot in said intermediate piece and said slot in said head piece, and wherein said take-up wheel is mounted to said second leg of said U-shaped member.

7. A dental floss tool, comprising:

a handle piece having a hollow interior and an open end;

an intermediate piece having a first end, a second end, and an intermediate portion therebetween, said first end of intermediate piece joined to said open end of said handle piece, said intermediate portion having a bore therein;

an actuator button slidingly fitted within said bore in said intermediate piece, said actuator button movable between a protruding position wherein an end of said actuator button perpendicularly protrudes from said intermediate piece and a flush position wherein said end of said actuator button is generally flush with said intermediate piece, said actuator button having a pair of grooves in opposite sides thereof and having a hole laterally therethrough, said hole interconnecting said pair of grooves, said hole exposed when said actuator button is in said protruding position and concealed when said actuator button is in said flush position;

a head piece having a first end and a second end, said first end of said head piece joined to said second end of said intermediate piece, said head piece including a pair of spaced tines extending from said second end thereof;

a spool of dental floss disposed within said hollow interior of said handle piece, a working length of said dental floss extending from said spool; and a tensioning means for holding said working length of said dental floss in tension, said working length of said dental floss extending out of said handle piece, extending along said intermediate piece through said hole in said actuator button, extending to said head piece, extending across said pair of spaced tines of said head piece, and extending back towards said intermediate piece to said tensioning means, a working section of said working length of said dental floss spanning said pair of spaced tines, a portion of said working length of said dental floss adjacent said hole in said actuator button fitting within each of said pair of grooves when said actuator button is moved to said flush position, said working section of said dental floss moving laterally in a first direction when said actuator button is moved to said flush position, said working section of said dental floss moving laterally in a second direction when said actuator button is moved to said protruding position, said second direction opposite said first direction.

8. The dental floss tool of claim 7, wherein said pair of spaced tines comprises a first tine and a second tine, said first tine and said second tine each including a shoulder extending therealong, said first tine and said second tine each having a tip end, said tip end having a notch therein, and wherein said working length of said dental floss extends down said first tine, abutting said shoulder thereof, passes through said notch in said tip end of said first tine, extends across to said second tine, passes through said notch in said tip end of said second tine, and extends up said second tine, abutting said shoulder thereof.

9. The dental floss tool of claim 7, wherein said intermediate piece includes a first neck portion at said first end and a second neck portion at said second end, said first neck portion open to said first end of said intermediate piece, said second neck portion open to said second end of said intermediate piece, said second neck portion having a slot therein, wherein said first neck portion of said intermediate piece fits within said open end of said handle piece and said second neck portion of said intermediate piece fits within said first end of said head piece, and wherein said head piece is open to said first end thereof, said head piece including a slot in said first end thereof, said slot in said head piece aligned and communicating with said slot in said second neck portion.

10. The dental floss tool of claim 9, wherein said first neck portion has a slot therein, said dental floss passing through said slot, and wherein said dental floss is captured between said handle piece and said intermediate piece.

11. The dental floss tool of claim 9, wherein said tensioning means comprises:

a spring assembly positioned within at least one of said intermediate piece and said head piece, and a take-up wheel coupled to said spring assembly.

12. The dental floss tool of claim 11, wherein said take-up wheel has a perimetrical groove therein, said working length of said dental floss wound around said take-up wheel within said perimetrical groove.

13. The dental floss tool of claim 12, wherein said take-up wheel includes a notch therein communicating with said perimetrical groove, said notch including a sharp edge for severing said dental floss.

14. The dental floss tool of claim 11, wherein said spring assembly comprises:

a torsional rod having a first end positioned within said second neck portion of said intermediate piece and a second end positioned within said first end of said head piece, said torsional rod including an arm, said arm extending through said slot in said second neck portion and said slot in said first end of said head piece, and wherein said take-up wheel is mounted to said arm.

15. The dental floss tool of claim 11, wherein said spring assembly comprises:

a helical compression spring disposed within said second end of said intermediate piece, said helical compression spring having a first end and a second end, said first end secured within said second end of said intermediate piece, and a generally U-shaped member having a first leg and a second leg, said first leg disposed within said second end of said intermediate piece and joined to said second end of said helical compression spring, said second leg extending through said slot in said second neck portion of said intermediate piece and said slot in said first end of said head piece, and wherein said take-up wheel is mounted to said second leg of said U-shaped member.

16. The dental floss tool of claim 11, wherein said spring assembly comprises:

a helical tension spring disposed within said first end of said head piece, said helical tension spring having a first end and a second end, said second end confined within said first end of said head piece, and a generally U-shaped member having a first leg and a second leg, said first leg disposed within said first end of said head piece and abutting said first end of said helical tension spring, said second leg extending through said slot in said second neck portion of said intermediate piece and said slot in said first end of said head piece, and wherein said take-up wheel is mounted to said second leg of said U-shaped member.

17. A dental floss tool, comprising:

an elongated member including a handle portion at one end and a head portion at an opposite end, said head portion including a pair of spaced tines extending therefrom;

a spool of dental floss disposed within said handle portion, a working length of said dental floss extending from said spool;

a tensioning means for holding said working length of said dental floss in tension, said tensioning means comprising a spring assembly mounted in association with at least one of said intermediate piece and said head piece and a take-up wheel coupled to said spring assembly;

said intermediate piece and said head piece each have a slot therein, said slot in said intermediate piece aligned and communicating with said slot in said head piece, wherein said spring assembly comprises a torsional rod having a first end positioned within said intermediate piece and a second end positioned within said head piece, said torsional rod including an arm. said arm projecting through said slot in said intermediate piece and said slot in said head piece. and wherein said take-up wheel is mounted to said arm;

said working length of said dental floss extending from said handle portion to said head portion spanning said pair of spaced tines and back to said tensioning means; and an actuator means for effectuating multidirectional movement of said working length of said dental floss.

18. The dental floss tool of claim 17, wherein said intermediate piece has a bore therein, wherein said actuator means comprises an actuator button slidingly fitted within said bore in said intermediate piece, said actuator button having a hole laterally therethrough, said actuator button being movable between a protruding position, wherein an end of said actuator button perpendicularly protrudes from said intermediate piece and a flush position wherein said end of said actuator button is generally flush with said intermediate piece, wherein said working length of said dental floss passes through said hole in said actuator button, and wherein said working length of said dental floss moves in a first direction when said actuator button is moved to said flush position and moves in a second direction when said actuator button is moved to said protruding position, said second direction opposite said first direction.

19. The dental floss tool of claim 17, wherein each of said pair of spaced tines includes a shoulder extending therealong, wherein each of said pair of spaced tines has a tip end, said tip end having a notch therein, and wherein said working length of said dental floss extends down a first of said pair of spaced tines so as to abut said shoulder thereof, through said notch in said tip end of said first of said pair of spaced tines, across to a second of said pair of spaced tines, through said notch in said tip end of said second of said pair of spaced tines, and up said second of said pair of spaced tines so as to abut said shoulder thereof.

* * * * *